(12) United States Patent
Grundei

(10) Patent No.: US 6,485,522 B1
(45) Date of Patent: Nov. 26, 2002

(54) ADAPTER FOR AN EXOPROSTHETIC STANDARD ELEMENT

(75) Inventor: Hans Grundei, Lubeck (DE)

(73) Assignee: Eska Implants GmbH & Co. (DE)

( * ) Notice: Subject to any disclaimer, the term of this patent is extended or adjusted under 35 U.S.C. 154(b) by 0 days.

(21) Appl. No.: 09/719,828

(22) PCT Filed: May 3, 1999

(86) PCT No.: PCT/EP99/02988
§ 371 (c)(1),
(2), (4) Date: Dec. 15, 2000

(87) PCT Pub. No.: WO99/65426
PCT Pub. Date: Dec. 23, 1999

(30) Foreign Application Priority Data

Jun. 17, 1998 (DE) .......................................... 198 26 638

(51) Int. Cl.$^7$ .................................................. A61F 2/80
(52) U.S. Cl. ........................................................ 623/38
(58) Field of Search .............................. 623/38, 27, 53, 623/32

(56) References Cited

U.S. PATENT DOCUMENTS

| 3,947,897 | A | | 4/1976 | Owens | |
|---|---|---|---|---|---|
| 4,143,426 | A | * | 3/1979 | Hall et al. | 623/56 |
| 4,158,895 | A | | 6/1979 | Reswick et al. | |
| 5,002,578 | A | * | 3/1991 | Luman | 623/23 |
| 5,041,137 | A | | 8/1991 | Nemoshkalov | |
| 5,759,206 | A | | 6/1998 | Bassett | |

FOREIGN PATENT DOCUMENTS

| DE | 31 25 268 | | 1/1983 |
|---|---|---|---|
| DE | 41 06 971 C1 | | 3/1992 |
| EP | 0 015 599 | | 9/1980 |
| JP | 01085645 | * | 3/1989 |

* cited by examiner

Primary Examiner—Corrine McDermott
Assistant Examiner—Alvin Stewart
(74) Attorney, Agent, or Firm—Cantor & Colburn LLP

(57) ABSTRACT

The invention relates an adapter for an exoprosthetic standard element such as an exoprosthetic knee joint. The adapter can be inserted with a proximal handle part into a tubular bone stump. The proximal handle part is at least partly covered with a tree-dimensional open-loop network structure and at its distal end has a coupling device for the standard element.

7 Claims, 1 Drawing Sheet

ADAPTER FOR AN EXOPROSTHETIC STANDARD ELEMENT

TECHNICAL FIELD

The invention concerns an adapter for an exoprosthetic standard part.

Different methods are known for exoprosthetic treatment of a patient who has had a limb amputated.

Thus it is conceivable to work exclusively with exoprosthetic shafts, for example prosthesis shafts, for example in the area of a thigh stump, which are adapted to the size and shapes of the thigh stump. Then in a given case an artificial exoprosthetic knee joint, a calf, as well as a foot, are connected with this prosthesis shaft.

In addition however, there are systems which are anchored with the remaining long bone stump ends so that more natural perceptive faculties, for example in the case of running, can be imparted to the patient. This is known under the name of osteoperception.

For this, for example, an adapter end with a thread is screwed into the remaining long bone, in order to be anchored with the latter. The adapter resembles a pipe piece, which finally emerges out of the tissue on the stump end. Then an exoprosthetic standard part, for example an artificial knee joint, is to be connected to this.

BACKGROUND OF THE INVENTION

In known adapters of the type described above, the stability of the fixation of the adapter in the long-bone stump is problematic, as is the coupling of a standard part.

An adapter is known from U.S. Pat. No. 3,947,897 that is inserted in the inter-medullary space of the femur, which is provided at its distal end with a coupling device for an exoprosthetic standard part. The seat in the intra-medullary space of the femur should be fixed by application of a bone cement, for example methyl methacrylate. Coupling of the standard part to the distal end should be accomplished by a kind of locking device.

Both the fixing with bone cement and the fixing of the standard part with the locking device are problematic.

Bone cement comes loose after a certain time. Also the locking device does not withstand a permanent seat for the exoprosthetic standard part.

SUMMARY OF THE INVENTION

With this background, it is the task of the present invention to provide an adapter for an exoprosthetic standard part that has a favorable long-time fixation behavior and is also permits the standard part to be replaced easily with another one, for example with advanced wear.

This task is solved by an adapter with the characteristics of claim 1.

Accordingly, it is recommended that the adapter be constructed in such a way that it can be inserted into a long-bone stump with a proximal stem part, whereby the stem part is covered, at least partly, by an open-mesh three-dimensional space-network structure and is provided at its other end with a coupling device for an exoprosthetic standard part, where the coupling device consists of a cone and an adapter sheath on it in the conical gluing seat, by which the exoprosthetic standard part is braced.

The open-mesh, three-dimensional space-network structure, which is also called inter-connecting, makes it possible for natural bone material to grow in, through, behind, and around it during the final healing phase, so that the stem part is integrated with the long bone with respect to the substrate flow within a relatively short time and an extremely stable secondary fixation is provided. The growth of bone material into an open-mesh three-dimensional space-network structure is known as such from pure endoprosthetics. We refer here to DE-PS 41 06 971, for example. But a fixation possibility is presented for the first time in the field of exoprosthetic care.

The coupling device provided on the distal side can then be seen freely in connection with the outstanding secondary fixation, because of the said space-network structure. Specifically, the lifetime of the adapter in the long-bone stump is so long, that external wear or breakage phenomena can appear that could no longer provide a precise seat for the exoprosthetic standard part at the coupling site.

The adapter sheath has the advantage of being replaceable, for example if the coupling of a standard part has:led to increased wear or breakage over the course of time. The adapter sheath itself can be replaced as whole.

The seat of the adapter sheath on the cone of the coupling device can also be secured by having a tension screw screwed through the adapter sheath into a threaded hole in the cone.

According to another advantageous variant, the stem part is provided with an surrounding flange for placement on the front edge of the long-bone stump. By this means, the adapter can be placed under stress directly after implantation of the stem part in the long-bone stump, specifically before sufficient bone materials have grown into the open-mesh three-dimensional space-network structure. The flange thus serves to receive the primary load of the forces appearing during the final healing phase and to direct the forces appearing to the cortex of the long-bone stump.

Preferably, the stem part connects, in the direction of the distal coupling device, to an intermediate piece which then runs from the end of the long-bone stump, through the body tissue, until the coupling device lies outside the body. At the site where the intermediate part comes out of the patient's body, there is then advantageously a sealing part on the intermediate piece. This sealing part protects the breakthrough site in the limb stump and contributes to the keeping the break-through site easier to keep aseptic. A barrier is thus constructed against severe inflammations that could progress farther into the limb stump.

The adapter described can be further developed advantageously so that the coupling device consists of a cone and an adapter sleeve resting on it in the conical clamping seat, with which sleeve the standard part can be clamped. This adapter sleeve has the advantage of being replaceable, perhaps when the connection of a standard part has led to increased wear or knocked-out pieces in the course of time. The adapter sleeve as such can be replaced as a whole.

The seating of the adapter sleeve on the cone of the coupling device also can be secured additionally by means of screwing a tightening screw through the adapter sleeve into a threaded hole in the cone.

According to an embodiment of the invention, the intermediate piece of the adapter can be adjusted in its length. This has the advantage that only one or a few sizes of the adapter according to the invention need to be manufactured and kept in storage. This reduces the costs significantly.

Alternatively, the intermediate piece consists of a metal mass, whereby stability is increased. Here, however, length adjustments are not possible, so that increased costs must be taken into account.

DESCRIPTION OF PREFERRED EMBODIMENTS

Figure 1:
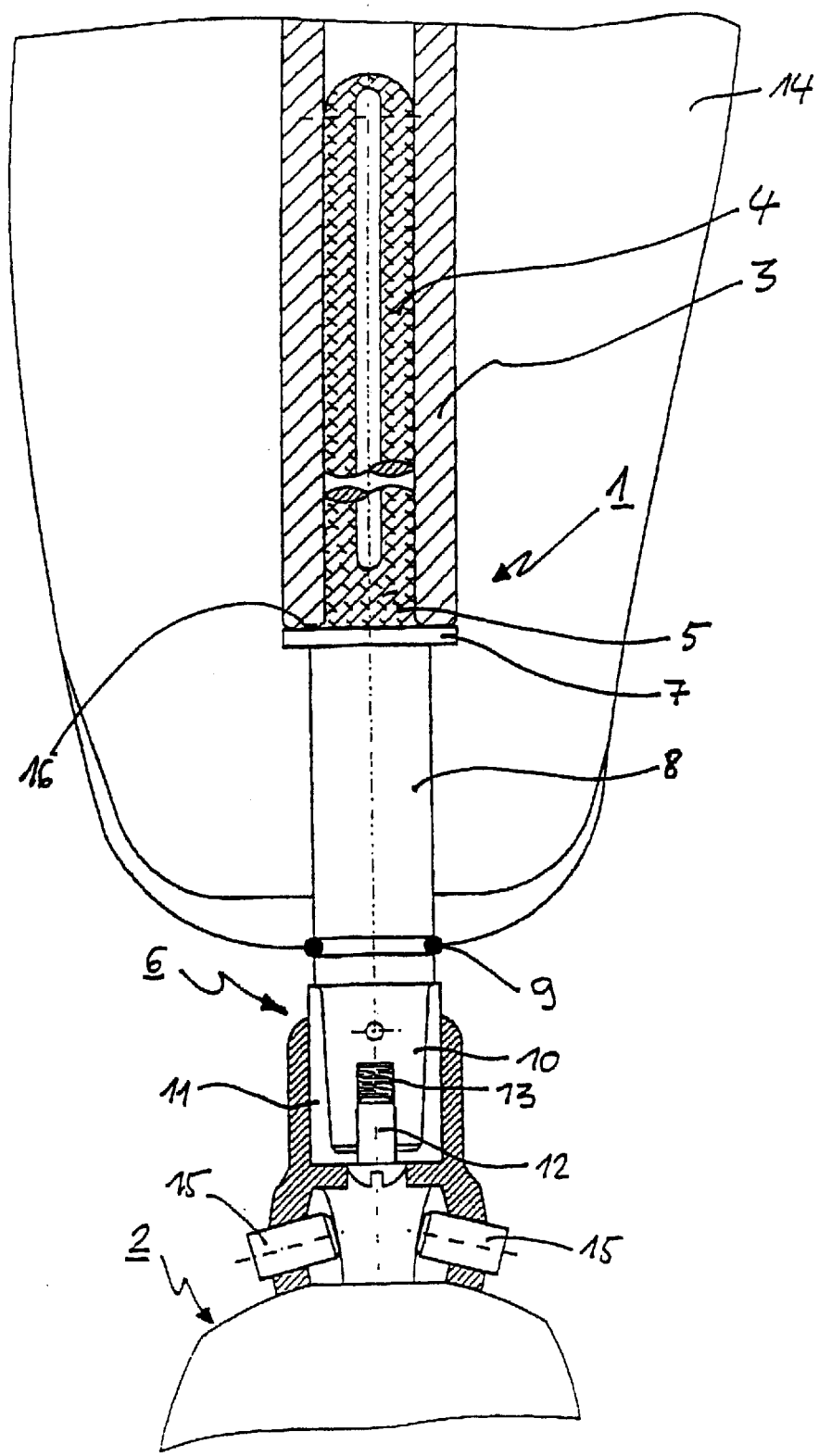
FIG. 1 discloses an adapter for an exprosthetic standard part.

This shows a schematic section of a thigh stump 14 with the femur stump 3. The stem part 4 of the adapter 1 is inserted into the long-bone femur stump 3. The surface of the stem part 4 is coated with an open-mesh three-dimensional space-network structure 5, through which bone materials can grow, so that the stem part 4, after a certain healing phase becomes part almost a component of the natural bone, as far as the substrate flow is concerned.

The stem part 4 is sealed on the distal side with a surrounding flange 7, which is fastened to the front edge 16 of the long bone stump 3. On the one hand this ensures primary loading capacity of the adapter 1 directly after the implantation, and, on the other hand, at least partially guiding loads which appear directly into the corticalis.

An intermediate piece 8, which in the present case is made of one piece of solid metal, is connected with the stem part 4, or, as the case may be, flange 7. The intermediate piece 8 is made large enough so that it can emerge out of the limb stump 14 on the distal side. The point of emergence in the present case is sealed with a surrounding sealing part 9 on the intermediate piece 8.

The intermediate piece 8 ends in a cone 10 of the coupling device 6. An adapter sleeve 11, the conical clamping seat of which additionally is secured on the cone 10 by a tightening screw 12, which is screwed through the adapter sleeve 11 into a threaded hole 13 in the cone 10, sits on the cone 10 in a conical clamping arrangement.

The coupling part 16, with which the exoprosthetic standard part 2 is connected by means of tightening screws 15, is inverted over the adapter sleeve 11.

If wear phenomena take place or parts of the sleeves are knocked out in the course of the wearing time, the adapter sleeve 11 can be replaced easily by unscrewing the tightening screw 12 out of the threaded hole 13, removing the adapter sleeve 11 from the cone 10, and replacing it with a new adapter sleeve 11. Then the exoprosthetic standard part can be remounted.

What is claimed is:

1. An adapter for an exoprosthetic standard part comprising:

a proximal stem part installed into a long bone stump;

an open-mesh three-dimensional space-network structure covering, at least partially, said stem part;

a coupling device provided on a distal end of said stem part for coupling with said exoprosthetic standard part;

wherein said coupling device includes a cone, an adapter sheath having a conical clamping seat, and a coupling part for connecting to said exoprosthetic standard part, said cone being seated in said conical clamping seat.

2. An adapter as in claim 1, wherein said conical clamping seat is secured to said cone by a tension screw which is screwed through said adapter sheath into a threaded hole formed in said cone.

3. An adapter as in claim 1, wherein said stem part includes a surrounding flange located at a front edge of said long-bone stump.

4. An adapter as in claim 1, further comprising an intermediate piece wherein said intermediate piece is connected to said stem part in the direction of said coupling device.

5. An adapter as in claim 4, further comprising a sealing part located on said intermediate piece at a position where said intermediate piece extends out of a body.

6. An adapter as in claim 4 wherein said intermediate piece can be adjusted in length.

7. An adapter as in claim 4 wherein said intermediate piece is of a metal mass.

* * * * *